May 6, 1975 A. B. COOK Plant Pat. 3,716

STRAWBERRY PLANT

Filed Nov 15, 1973

United States Patent

Plant Pat. 3,716
Patented May 6, 1975

3,716

STRAWBERRY PLANT

Albert B. Cook, R.R. 1, Box 191,
Grandview, Ind. 47615

Filed Nov. 15, 1973, Ser. No. 416,294
Int. Cl. A01h *5/03*
U.S. Cl. Plt.—48 1 Claim

My invention relates to a new and distinct variety of strawberry plant. It is the result of a cross of (Canall × Twentieth Century) × Twentieth Century, made by me in 1964, at Grandview, Ind.

Since my discovery of the original plant, I have asexually reproduced a large number of plants from the original mother plant by rooted runners.

My object in the asexual propagation of the original mother plant was to determine the characteristics of the plant and of its fruit by the testing of a large number of plants. The distinguishing features of my new variety have proved to be permanent. My new variety has proved itself to have unusual possibilities because of its extremely vigorous growth; its very tall plants; its very long runners; its very large leaves; and its very large fruit, which has an unusual and a high flavor.

Figure 1:
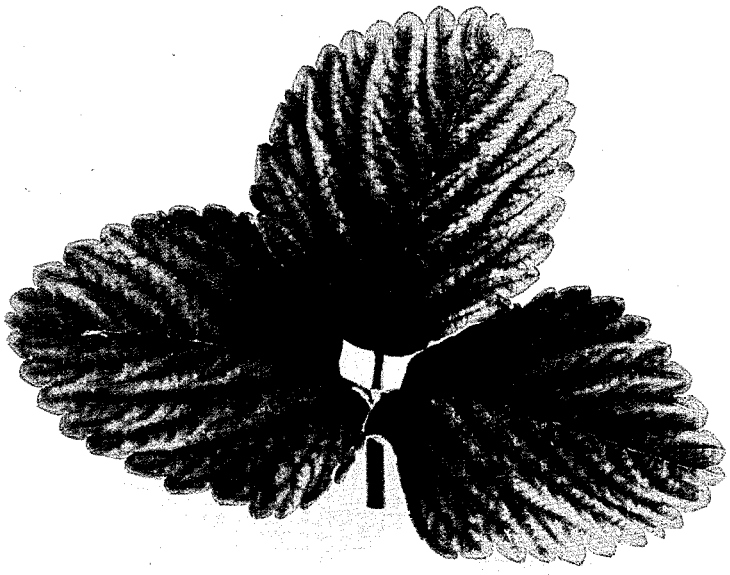
FIG. 1 shows a typical leaf in full color.
Figure 2:
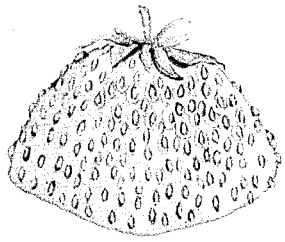
FIG. 2 is a berry of typical shape.

In general, the distinct and new variety of strawberry plant, which is the subject of my invention and discovery, is characterized by its extremely vigorous growth; by its very tall plants; by its very long runners; by its very large leaves; and by its very large fruit, which has an unusual and a high flavor. These characteristics I now refer to in greater detail. Color plate references are according to Color Standards and Color Nomenclature by Robert Ridgway.

Under the conditions at Grandview, Ind., and at Champaign, Ill., my new variety of plant is June-bearing and low to medium in productivity. The plants are extremely vigorous, very large, and very tall, measuring up to 15 inches in height and averaging about 11 to 12 inches. They produce a medium number of runners, but make a very wide row. The internodes are thick and very long, measuring up to 30 inches in length and averaging about 12 to 18 inches.

The leaves are light green to yellowish green in color, or are approximately Lettuce Green (Plate V), or varying from Spinach Green (Plate V) to Lettuce Green (Plate V) to Cosse Green (Plate V), depending mainly on soil fertility, but also depending on other soil conditions, exposure, and weather and climatic conditions. The leaves are very large (up to 9 inches in width and averaging about 6 to 7 inches), slightly glossy to glossy, slightly cupped, and rugose. The terminal leaflet slightly overlaps the lateral leaflets, and the lateral leaflets overlap at the base of the leaf. The flowers are pistillate. Two patented varieties with very large berries, Mildred Felten (Plant Pat. No. 761) and Lustre (Plant Pat. No. 929), have perfect flowers. The date of the first blossoms in 1973 at Champaign, Ill., was May 6.

At Grandview, Ind., and at Champaign, Ill., my new variety of strawberry plant begins to mature its fruit late, about 2 to 3 days later than Jerseybelle. Two patented varieties with very large berries. Mildred Felten and Lustre, are midseason varieties. The date of the first picking in 1973 at Champaign, Ill., was June 5. The harvesting period is medium in length. Usually, only the primary and secondary berries are well formed and large enough to harvest.

The fruit is medium dark red and very slightly purplish, or is approximately Amaranth Purple (Plate XII), or varying from Pomegranate Purple (Plate XII) to Amaranth Purple (Plate XII) to Pansy Purple (Plate XII), depending mainly on exposure, but also depending on soil, weather, and climatic conditions. The fruit is very large (up to 2½ inches in diameter and averaging about 1½ to 2 inches), wedge to irregular in shape, slightly glossy to glossy, and firm. The fruit stems are thick.

The calyx is medium in size. The achenes are raised, and are yellow to red depending on exposure.

Under the conditions existing where I have reproduced and tested my new variety of strawberry plant, the flesh of the berry is medium red and slightly purplish and is firm with no noticeable core. The fruit is relatively sweet, and has an unusual and a high flavor.

The strawberry above described, and the plant producing it, of course, may vary in slight details, depending on soil, weather, and climatic conditions.

What I claim is:

1. A new and distinct variety of strawberry plant substantially as herein shown and described, characterized by its extremely vigorous growth; by its very tall plants; by its very long runners; by its very large leaves; and by its very large fruit, which has an unusual and a high flavor.

References Cited

UNITED STATES PATENTS

| | | | | |
|---|---|---|---|---|
| P.P. | 761 | 9/1947 | Felten | Plants—48 |
| P.P. | 929 | 3/1950 | Felten | Plants—48 |

ROBERT E. BAGWILL, Primary Examiner